United States Patent [19]

Neumann et al.

[11] Patent Number: 5,859,296
[45] Date of Patent: Jan. 12, 1999

[54] PROCESS FOR ISOLATING HYDROXYPIVALIC ACID FROM AQUEOUS SOLUTION

[75] Inventors: Karl Heinz Neumann, Sankt Augustin; Dieter Heitkamp, Burscheid; Helmut Fiege, Leverkusen, all of Germany

[73] Assignee: Bayer Aktiengesellschaft, Leverkusen, Germany

[21] Appl. No.: 906,322

[22] Filed: Aug. 5, 1997

[30] Foreign Application Priority Data

Aug. 16, 1996 [DE] Germany ............... 196 32 924.8

[51] Int. Cl.⁶ ..................................................... C07C 51/42
[52] U.S. Cl. ............................................................ 562/580
[58] Field of Search ............................................. 562/580

[56] References Cited

U.S. PATENT DOCUMENTS

| 2,285,886 | 6/1942 | Beck et al. | 562/580 |
| 3,716,584 | 2/1973 | Chaintron | 562/580 |
| 3,799,977 | 3/1974 | Rutledge | 260/531 |
| 4,431,486 | 2/1984 | Balmut | 203/69 |
| 5,104,492 | 4/1992 | King et al. | 203/15 |

FOREIGN PATENT DOCUMENTS

| 43-024888 | 10/1968 | Japan . | |
| 43-24888 | 10/1968 | Japan . | |
| 53-077010 | 12/1976 | Japan | B01J 23/44 |

OTHER PUBLICATIONS

H.P. Frank, et al., Über die Herstellung von Hydroxypivalinsäure und deren Polyester, Monatshefte für Chemie, 95, pp. 410–414, (1964).

H. Frank, et al., "Preparation of Hydroxypivalic Acid and Its Polyesters", Monatsh., 95, (2), 410–14, (1964), (abstract only from CA 61,12099).

F. Nerdel, et al., Zur Bildung eines 2–Alkoxy–azetidins, Chem. Ber. 102,(5) pp. 1606–1609, (1969).

E.T. Stiller, et al., Panthothenic Acid. VIII. The Total Synthesis of Pure Pantothenic Acid, vol. 62, pp. 1785–1790, (Jul. 1940).

*Primary Examiner*—Gary Geist
*Assistant Examiner*—Rosalynd Keys
*Attorney, Agent, or Firm*—Sprung Kramer Schaefer & Briscoe

[57] ABSTRACT

Hydroxypivalic acid is obtained from aqueous solutions by removal of the water by azeotropic distillation and subsequent crystallization from a solvent mixture which is composed of a polar and a non-polar component. The distillation is carried out under reduced pressure and at a maximum bottom temperature of 90° C., until a residual water content of at least 0.1% of the total weight of the resulting solution is achieved.

16 Claims, No Drawings

PROCESS FOR ISOLATING HYDROXYPIVALIC ACID FROM AQUEOUS SOLUTION

BACKGROUND OF THE INVENTION

1. Field of the Invention

The invention relates to a process for isolating hydroxypivalic acid from aqueous solution by removal of the water by azeotropic distillation under reduced pressure using an organic solvent or solvent mixture suitable for this, and subsequent crystallization of the hydroxypivalic acid from an organic solvent mixture which is composed of a polar and a non-polar component, one or both components of which have been employed in the preceding azeotropic distillation.

2. Description of the Related Art

In addition to potassium permanganate oxidation of neopentylglycol and Cannizzarro reaction of hydroxypivalaldehyde, both of which are relatively unattractive from the industrial aspect, hydroxypivalic acid can be prepared by air/$O_2$ oxidation of neopentylglycol or by $H_2O_2$ oxidation of hydroxypivalaldehyde. The oxidation of neopentylglycol with $O_2$ or air over a Pd/C or Pt/C catalyst in alkaline aqueous solution to give hydroxypivalic acid is described, for example, in JP 53/77 010 or in U.S. Pat. No. 3,799,977. In both patents, no instructions are given for liberation of the hydroxypivalic acid obtained as the Na salt. Furthermore, the yield and selectivity data are lacking completely in U.S. Pat. No. 3,799,977, and a very dubious yield of 100% based merely on the comparison of IR bands of the sodium hydroxypivalate prepared according to JP 53/77 010 with a pure sodium hydroxypivalate sample is stated in JP 53/77 010. As an alternative to this process, hydroxypivalic acid can also be synthesized by oxidation of hydroxypivalaldehyde with hydrogen peroxide. This process was described for the first time in Monatshefte für Chemie 95, (1964), 410 and taken up again in an improved variant in 1968 in JP 43/24 888. After the hydrogen peroxide oxidation, the hydroxypivalic acid is obtained in aqueous solution. For isolation, according to Monatshefte, the hydroxypivalic acid is converted into the Na salt by addition of $Na_2CO_3$. This salt is precipitated by addition of 10 times the volume of acetone and is filtered off. The residue is dissolved in a little water and the hydroxypivalic acid is liberated with the stoichiometric amount of $H_2SO_4$ and taken up in $CHCl_3$. The water-moist $CHCl_3$ solution is dried with $Na_2SO_4$, the $Na_2SO_4$ is filtered off and the $CHCl_3$ is evaporated off. A crude hydroxypivalic acid having a melting range of 100° to 122° C. (literature: 124°–126° C.) remains. This wide melting range indicates that the hydroxypivalic acid contains a considerable amount of entrained impurities. Assuming the crude hydroxypivalic acid according to the Monatshefte is pure, the hypothetical yield is about 69% of the theoretical yield, based on the hydroxypivalaldehyde employed. The authors obtain truly pure hydroxypivalic acid having a melting point of 125° to 126° C. only after further crystallizations, first from $CHCl_3$ and then from water. Since hydroxypivalic acid has an excellent water-solubility, it must be assumed that the yield of pure hydroxypivalic acid after these further recrystallizations falls significantly below 50% of the theoretical yield. The increase in volume due to the addition of acetone and the large number of working-up steps also make this process unattractive industrially.

JP 43/24 888 now describes a variant of the above process using a catalyst which is capable of dissociating hydrogen peroxide. Very fine particles of gold, platinum, silver or glass and also UV light of wavelength 2000 to 4000 Å are mentioned as such catalysts. The difficulties of obtaining hydroxypivalic acid by crystallization from aqueous solution are dealt with further in this patent application; no material which has a melting point above 120° C. was to be isolated from water. The authors therefore remove the water completely by azeotropic distillation with a suitable solvent, such as benzene, toluene, cyclohexane, n-butanol and the like; however, only benzene is employed in the patent examples. After the dehydration, the solvent is stripped off and the crude hydroxypivalic acid is subjected to fractional distillation under reduced pressure. During reworking of Example 2 from JP 43/24 888 with toluene instead of benzene (for industrial hygiene reasons), the water was distilled off azeotropically. In the subsequent distillation of hydroxypivalic acid, only 0.64 mol of the 2.35 mol of hydroxypivalic acid originally present in the solution could be distilled off under 20 mbar. Bifunctional hydroxypivalic acid forms polyesters and anhydrides during distillation, which remain as a dark brown distillation residue. The distillate must furthermore be kept in the melt at approx. 125° C. This can also lead to losses in yield and quality due to oligo-/polymerization reactions. The hydroxypivalic acid distillate must then still be cooled on a belt and comminuted mechanically.

Alternatively, after the azeotropic dehydration, the hydroxypivalic acid is crystallized out of the entraining agent benzene according to JP 43/24 888 by cooling, but must be recrystallized from benzene again in order to achieve the required quality.

Since benzene is classified as carcinogenic, crystallization from this solvent is now regarded as unacceptable from the industrial hygiene aspect. Our own works have shown that after azeotropic dehydration of an oxidation batch with the less unacceptable toluene, subsequent crystallization from the solvent led to a tacky hydroxypivalic acid having a content of less than 95% (GC); this is evidently to be attributed to the abovementioned entrained impurities.

The processes described to date for isolation of hydroxypivalic acid are not very suitable for industrial preparation of hydroxypivalic acid because of the number of working-up steps and the marked tendency to form polyesters/anhydride at higher temperatures.

SUMMARY OF THE INVENTION

It has now been found, surprisingly, that firstly the procedure must take place under reduced pressure for removal of the water, secondly the removal of the water must not be carried out to complete dryness, and thirdly the crystallization of the hydroxypivalic acid can be improved by combination of a non-polar organic solvent with a polar organic solvent to the extent that the hydroxypivalic acid is already obtained with a purity of at least 98.0% in the first crystallization. A further purification operation, such as distillation of the hydroxypivalic acid or renewed crystallization, is superfluous as a result.

The invention relates to a process for isolating hydroxypivalic acid from aqueous solutions by removal of the water by azeotropic distillation and subsequent crystallization of the hydroxypivalic acid from an organic solvent, which comprises (a) adding one or more organic solvents, of which at least one forms an azeotrope with water, to the aqueous solution, (b) distilling off the water under reduced pressure until the resulting solution of the hydroxypivalic acid in the organic solvent(s) has a residual water content of at least 0.1% by weight, based on the total weight of the solution formed, and (c) adjusting the solution formed such that it comprises at least one polar and at least one non-polar solvent and the hydroxypivalic acid crystallizes out of it.

DETAILED DESCRIPTION OF THE INVENTION

Non-polar solvents for the crystallization are, for example, aliphatic and aromatic $C_6$–$C_{10}$-hydrocarbons, such as benzene, toluene, xylene, ethylbenzene, cyclohexane, n-hexane, methylcyclohexane or a mixture of several of these.

Polar solvents for the crystallization are, for example $C_1$–$C_6$-alcohols, esters having 3–10 C atoms in total, $C_3$–$C_8$-ketones, $C_4$–$C_{10}$-ethers, $C_3$–$C_6$-nitriles or a mixture of several of these, such as methanol, ethanol, n- or i-propanol, n- or i-butanol, pentanol, hexanol, ethyl acetate, isopropyl acetate, i- or n-butyl acetate, 1-methoxy-2-propyl acetate, methyl ethyl ketone, methyl isobutyl ketone, methyl tert-butyl ether, diisopropyl ether, acetonitrile or a mixture of several of these.

The mixture of at least one non-polar and at least one polar solvent employed for the crystallization in the process according to the invention comprises at least one solvent which forms an azeotrope with water, and is therefore already employed in azeotropic distillation. Azeotrope-forming solvents are to be found both in the group of non-polar solvents and in that of polar solvents. In the case where a non-polar solvent has been used for the azeotropic distillation, a polar solvent is subsequently added to adjust the resulting solution for the crystallization, and vice versa. It is of course also possible to use several solvents from each group; however, this is less preferable because of the complicated working up. It is of course also possible for a mixture of at least one polar and at least one non-polar solvent, of which at least one forms an azeotrope with water, already to be employed for the azeotropic distillation and for the adjustment of the resulting solution for the crystallization to be anticipated.

The two solvent combinations toluene/1-butanol and cyclohexane/n-butyl acetate have proved to be particularly suitable. Solvent mixtures of the following composition are preferably employed here for the crystallization: 95 to 40 parts by volume of toluene and 5 to 60 parts by volume of 1-butanol, or 80 to 30 parts by volume of n-butyl acetate and 20 to 70 parts by volume of cyclohexane.

Solvent combinations of 95 to 75 parts by volume of toluene and 5 to 25 parts by volume of 1-butanol, or 75 to 50 parts by volume of n-butyl acetate and 25 to 50 parts by volume of cyclohexane are particularly preferably employed.

It is a further feature that the removal of water by azeotropic distillation is carried out under a reduced pressure of 10–500 mbar, preferably 30–400 mbar. It is of course possible to remove some of the water, for example 10–70% of the total amount of water, in a simple distillation before the addition of the azeotrope-forming agent and before entry into the azeotropic distillation, this also being carried out under the reduced pressure stated.

The removal of the water is carried out up to a point at which at least 0.1% by weight of water, based on the total weight of the solution formed, is still present in the resulting solution of hydroxypivalic acid, for example 0.1–2% by weight, preferably 0.5–1.5% by weight.

The process is carried out, for example, by oxidizing hydroxypivalaldehyde, which has been prepared, for example, by condensation of isobutyraldehyde with formaldehyde under trialkylamine catalysis, with $H_2O_2$ to give hydroxypivalic acid. As an alternative to the trialkylamine catalyst, other bases, such as, for example, $Na_2CO_3$ (JP 43/24888) or NaOH or KOH (J. Am. Chem. Soc. 62 (1940), 1785; Chem. Ber. 102 (1969), 1606) can also be employed in the aldehyde condensation. The aqueous hydroxypivalic acid solution obtained is brought, for example, to pH=2.5, generally to pH=2–4, with mineral acid, and about half of the amount of water present in the solution is then distilled off under reduced pressure. The organic solvent or solvent mixture which forms an azeotrope with water is then added, and the remaining water is removed from the solution by azeotropic distillation under reduced pressure down to a residual content of about 1% by weight. Over-dehydration, for example to below 0.1% by weight of water in the distillation bottom product, must be carefully avoided, since otherwise oligomers and/or anhydrides of hydroxypivalic acid can form.

Both the solvent which forms an azeotrope with water, such as toluene, by itself and the solvent mixture, for example of toluene and 1-butanol, can be employed in the dehydration. The same also applies to other combinations, for example of n-butyl acetate or cyclohexane; each of the components (polar or non-polar) can be employed for the dehydration by itself or as a solvent mixture. For the quality of the hydroxypivalic acid, it is of preferred importance for the azeotropic dehydration to take place under reduced pressure and for a bottom temperature of 90° C., particularly preferably 65° C., not to be exceeded here. If dehydration is carried out under normal pressure, a yellow coloration of the bottom product occurs, which comes through to the crystallized product. For the crystallization, the second solvent is added, if it has not already been employed for the dehydration. The product-containing solution is then preferably cooled down to −18° C., for reasons of costs particularly preferably down to −8° C., since brines are usually available as coolants in industrial production. The hydroxypivalic acid crystals are filtered off, washed with the solvent mixture and dried at a maximum of 60° C. under reduced pressure in a drying cabinet.

The following examples are intended to illustrate but in no way limit the subject matter of the invention.

EXAMPLE 1

(for comparison)

1600 g of a hydroxypivalic acid solution originating from an $H_2O_2$ oxidation and having an acid content of 36.95% by weight were initially introduced into a 4 l four-necked flask with a stirrer, internal thermometer and water separator, and 1 l of toluene was added. The solution was dehydrated azeotropically under normal pressure, starting at a bottom temperature of 85° C. up to a bottom temperature of 110° C. During the dehydration, a yellowish discoloration of the reaction solution occurred. The residual water content was ~1.3% by weight, according to Karl Fischer titration. The solution was first cooled rapidly, while stirring, until crystallization starts at 40° C., and was then cooled further at 10° C./hour down to 0° C. The hydroxypivalic acid crystals were filtered off with suction, washed with 200 ml of toluene and dried at 150 mbar/55° C. in a drying cabinet. 503.9 g of hydroxypivalic acid having a content of 91.31% (GC internal standard)=77.8% of the hydroxypivalic acid present in the starting solution were obtained. This example shows that azeotropic dehydration with toluene by itself under normal pressure and subsequent crystallization leads to an unsatisfactory hydroxypivalic acid quality.

EXAMPLE 2

(for comparison)

1279 g of a 36.95% strength aqueous hydroxypivalic acid solution originating from an $H_2O_2$ oxidation were initially introduced into the apparatus described in Example 1, and 662 ml of n-butyl acetate and 500 ml of cyclohexane were added. The solution was dehydrated azeotropically under normal pressure down to a residual $H_2O$ content of 0.14% by weight, according to Karl Fischer titration. During the dehydration, the solution became yellowish in color. The organic hydroxypivalic acid solution was cooled rapidly to 60° C. and then cooled further at 10° C./hour to −5° C., and was stirred overnight at −5° C. The hydroxypivalic acid crystals were filtered off with suction, washed twice with in each case 133 ml of the solvent mixture and dried at 150 mbar/60° C. in a drying cabinet 367.2 g of hydroxypivalic acid having a content of 92.1% (GC internal standard)= 71.6% of the hydroxypivalic acid present in the starting solution were obtained. This example shows that azeotropic dehydration under normal pressure does not lead to the required product quality even if a solvent mixture is used.

EXAMPLE 3

1931 g of an aqueous hydroxypivalic acid solution originating from an $H_2O_2$ oxidation and having a hydroxypivalic acid content of 36.95% were initially introduced into the apparatus described in Example 1, and 515 g of water were distilled off at an overhead temperature of about 40° C./60 to 70 mbar. The distillation device was replaced by a water separator and 1000 g of n-butyl acetate and 500 g of cyclohexane were added to the receiver. A further 286 g of water were distilled off azeotropically under 160 to 180 mbar/bottom temperature of 40° to 45° C. The dehydration was interrupted at a residual water content of 1% by weight (according to Karl Fischer titration). The hydroxypivalic acid solution was transferred to a 2 l double-walled sulfonating beaker with a stirrer and internal thermometer, which was temperature-controllable with a cryostat. The solution was cooled rapidly to 50° C. and then cooled further from 50° C. to −5° C. in the course of 4 hours. It was stirred at −5° C. for a further hour, and the crystallized hydroxypivalic acid was then filtered off with suction and washed twice with 200 ml of solvent mixture cooled to −5° C. each time. After air had been sucked through the filter cake for 15 minutes, the hydroxypivalic acid was dried overnight in a drying cabinet under 200 mbar/60° C. 544 g of hydroxypivalic acid having a content of 98.0% (GC internal standard), which corresponded to 74.7% of the hydroxypivalic acid present in the starting solution, were obtained.

EXAMPLE 4

1892 g of an aqueous hydroxypivalic acid solution originating from an $H_2O_2$ oxidation and having a hydroxypivalic acid content of 37.5% by weight were initially introduced into the apparatus described in Example 1, and 432.4 g of water were distilled off under 62 to 66 mbar/bottom temperature of 37° to 45° C. The distillation device was then replaced by a water separator. 1285 ml of toluene and 215 ml of 1-butanol were added and a further 418 g of water were distilled off azeotropically under 130 to 300 mbar/bottom temperature of 40° to 60° C. The solution then had a residual water content of 0.8% according to Karl Fischer titration. The hydroxypivalic acid solution was transferred to a 2 l double-walled sulfonating beaker with a stirrer and internal thermometer, which was temperature-controllable with a cryostat. The solution was cooled rapidly to 40° C. and then cooled further at 10° C./hour to −5° C. It was stirred at −5° C. for a further hour to bring the crystallization to completion, and the hydroxypivalic acid which had crystallized was then filtered off with suction on a cooled glass suction filter. Air was sucked through the filter cake for 10 minutes and the cake was then washed twice with 200 ml of cold solvent mixture at −5° C. each time. The hydroxypivalic acid crystals were dried under 150 mbar/30° C. in a drying cabinet. 504 g of hydroxypivalic acid having a content of >99.9% (GC internal standard), which corresponded to 71.1% of the amount of hydroxypivalic acid present in the oxidation solution, were obtained; melting point: 126° to 127° C.

What is claimed is:

1. A process for isolating hydroxypivalic acid from aqueous solutions by removal of the water by azeotropic distillation and subsequent crystallization of the hydroxypivalic acid from an organic solvent, which comprises (a) adding one or more organic solvents, of which at least one forms an azeotrope with water, to the aqueous solution, (b) distilling off the water under reduced pressure until the resulting solution of the hydroxypivalic acid in the organic solvent(s) has a residual water content of at least 0.1% by weight, based on the total weight of the solution formed, and (c) adjusting the solution formed such that it comprises at least one polar and at least one non-polar solvent and the hydroxypivalic acid crystallizes out of it.

2. The process of claim 1, wherein a non-polar solvent from the group consisting of aliphatic and aromatic $C_6$–$C_{10}$-hydrocarbons or a mixture of several of these is employed.

3. The process of claim 2, wherein the non-polar solvent is one or several of the group consisting of benzene, toluene, xylene, ethylbenzene, cyclohexane, n-hexane and methylcyclohexane.

4. The process of claim 1, wherein a polar solvent from the group consisting of $C_1$–$C_6$-alcohols, esters having 3 to 10 C atoms in total, $C_3$–$C_8$-ketones, $C_4$–$C_{10}$-ethers and $C_3$–$C_6$-nitriles or a mixture of several of these is employed.

5. The process of claim 4, wherein the polar solvent is of the group of methanol, ethanol, n- or i-propanol, n- or i-butanol, pentanol, hexanol, ethyl acetate, isopropyl acetate, i- or n-butyl acetate, 1-methoxy-2-propyl acetate, methyl ethyl ketone, methyl isobutyl ketone, methyl tert-butyl ether, diisopropyl ether and acetonitrile or a mixture of several of these.

6. The process of claim 1, wherein, in the mixture of a non-polar and a polar solvent, at least one forms an azeotrope with water.

7. The process of claim 1, wherein the mixture of a non-polar and a polar solvent comprises toluene and 1-butanol, or n-butyl acetate and cyclohexane.

8. The process of claim 7, wherein a mixture of 95 to 40 parts by volume of toluene and 5 to 60 parts by volume of 1-butanol, or 80 to 30 parts by volume of n-butyl acetate and 20 to 70 parts by volume of cyclohexane is used.

9. The process of claim 8, wherein a mixture of 95 to 75 parts by volume of toluene and 5 to 25 parts by volume of 1-butanol or 75 to 50 parts by volume of n-butyl acetate and 25 to 50 parts by volume of cyclohexane is used.

10. The process of claim 1, wherein the azeotropic dehydration is carried out under reduced pressure such that a bottom temperature of 90° C. is not exceeded.

11. The process of claim 10, wherein a bottom temperature of 65° C. is not exceeded.

12. The process of claim 1, wherein the residual water content in the bottom product does not fall below 0.1% by weight during the azeotropic dehydration.

13. The process of claim 1, wherein the product-containing solvent mixture is cooled down to −18° C. for crystallization of the hydroxypivalic acid.

14. The process of claim 13, wherein the solvent mixture is cooled down to −8° C.

15. The process of claim 1, wherein the hydroxypivalic acid crystals are isolated by filtration and dried at a maximum of 60° C. under reduced pressure.

16. The process of claim 1, wherein hydroxypivalic acid which is obtained by condensation of isobutyraldehyde with formaldehyde under trialkylamine catalysis and subsequent $H_2O_2$ oxidation is employed.

* * * * *